United States Patent [19]

Chou et al.

[11] Patent Number: 4,638,088

[45] Date of Patent: Jan. 20, 1987

[54] PESTICIDAL BIPHENYLYLOXY AND BIPHENYLYLALKOXY ARYL ACYL UREA COMPOUNDS

[75] Inventors: David T. Chou; Robert C. Ligon, both of Raleigh, N.C.

[73] Assignee: Union Carbide Corporation, Danbury, Conn.

[21] Appl. No.: 672,007

[22] Filed: Nov. 15, 1984

[51] Int. Cl.$^4$ ............... C07C 127/22; C07C 157/12; C07C 143/833; C07C 149/40
[52] U.S. Cl. ..................... 564/23; 564/44; 562/439; 562/432; 560/18; 560/34; 558/412; 558/417
[58] Field of Search .............. 564/23, 44; 562/439, 562/432; 560/18, 34; 260/465 E; 558/412, 417

[56] References Cited

U.S. PATENT DOCUMENTS

| | | | |
|---|---|---|---|
| 3,748,356 | 7/1973 | Wellinga et al. | 564/23 |
| 4,005,223 | 1/1977 | Sirrenberg et al. | 564/44 |
| 4,194,005 | 3/1980 | Sirrenberg et al. | 564/522 |
| 4,276,310 | 6/1981 | Sirrenberg et al. | 564/23 |
| 4,350,706 | 9/1982 | Brouwer | 564/44 |
| 4,426,385 | 1/1984 | Cain | 564/44 |
| 4,533,676 | 8/1983 | Sirrenberg et al. | 564/535 |

FOREIGN PATENT DOCUMENTS

| | | | |
|---|---|---|---|
| 0057888 | 8/1982 | European Pat. Off. | 564/44 |
| 0093977 | 11/1983 | European Pat. Off. | 564/44 |
| 3104407 | 8/1982 | Fed. Rep. of Germany | 564/44 |
| 2531202 | 12/1982 | Fed. Rep. of Germany | 564/44 |
| 3217619 | 11/1983 | Fed. Rep. of Germany | 564/44 |

*Primary Examiner*—Charles F. Warren
*Assistant Examiner*—R. A. Picard
*Attorney, Agent, or Firm*—Gerald L. Coon

[57] ABSTRACT

Novel biphenylyloxy and biphenylylalkoxy aryl acyl urea compounds are provided together with methods for their preparation and the use of said compounds as the active toxicant in pesticidal compositions.

22 Claims, No Drawings

PESTICIDAL BIPHENYLYLOXY AND BIPHENYLYLALKOXY ARYL ACYL UREA COMPOUNDS

BRIEF SUMMARY OF THE INVENTION

1. Technical Field

This invention relates to novel biphenylyloxy and biphenylylalkoxy aryl acyl urea compounds which are useful as the active toxicant in pesticidal compositions. This invention also relates to a method for the preparation of the novel biphenylyloxy and biphenylylalkoxy aryl acyl urea compounds. This invention further relates to pesticidal compositions and to a method for their use.

2. Background of the Invention

In recent years a variety of polycyclic urea compounds have been reported in the literature as having pesticidal activity. For example, German Patent application No. DE 3,217,619 published Nov. 17, 1983 discloses phenylphenoxy aryl 2,4-dihalobenzoyl urea compounds and their use as pesticides. Also, European Patent Application Publication No. 0093977 published Nov. 16, 1983 discloses phenylphenoxy aryl 2,5-dihalobenzoyl urea compounds having utility as pesticides. N-benzoyl-N'-(phenoxyphenoxyphenyl) urea compounds have been disclosed in German Patent Application No. DE 3,104,407 published Aug. 19, 1982 and European Patent Application Publication No. 0057888 published Aug. 18, 1982. Such compounds are indicated therein to possess pesticidal properties. Bicyclooxyaryl benzoyl urea compounds in which the bicyclooxy group is a fused ring system which is attached to oxygen through a carbocyclic ring, e.g., naphthoxy, have been disclosed for example in U.S. Pat. No. 4,426,385 issused Jan. 17, 1984. Such compounds are indicated therein to be useful as pesticides.

Accordingly, one or more of the following objects will be achieved by the practice of this invention. It is an object of this invention to provide novel biphenylyloxy and biphenylylalkoxy aryl acyl urea compounds which exhibit outstanding pesticidal activity. Another object of this invention is to provide methods or processes for the preparation of the novel polycyclic urea compounds. A further object is to provide novel pesticidal compositions containing the novel biphenylyloxy and biphenylylalkoxy aryl acyl urea compounds as the active toxicant. A still further object of this invention is to provide a method for controlling pests by the application of the novel pesticidal compositions. These and other objects will readily become apparent to those skilled in the art in light of the teachings herein set forth.

DISCLOSURE OF THE INVENTION

This invention relates to novel biphenylyloxy and biphenylylalkoxy aryl acyl urea compounds, pesticidal compositions thereof, and a process for their preparation and use. The polycyclic urea compounds of this invention are those represented by the following generic formula:

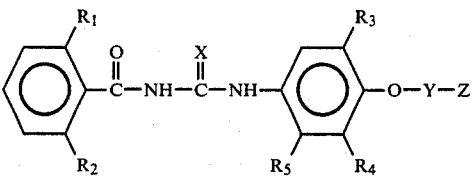

wherein: $R_1$, $R_2$, $R_3$, $R_4$, $R_5$, X, Y and Z are as hereinafter described.

DETAILED DESCRIPTION

As indicated above, the novel biphenylyloxy and biphenylylalkoxy aryl acyl urea compounds of this invention are conveniently represented by the following formula:

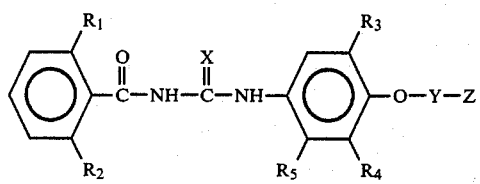

wherein:

$R_1$ is halogen, $C_{1-6}$ alkyl, alkoxy, polyhaloalkyl, polyhaloalkoxy or nitro;

$R_2$ is hydrogen, halogen, $C_{1-6}$ alkyl, alkoxy, polyhaloalkyl, polyhaloalkoxy or nitro;

$R_3$, $R_4$ and $R_5$ are independently hydrogen, halogen, $C_{1-6}$ alkyl, alkoxy, polyhaloalkyl, polyhaloalkoxy, nitro, cyano, carboxylic acid, carboxylic acid salt or carboxylic acid ester;

X is oxygen or sulfur;

Y is $C_{1-8}$ alkylene or a covalent bond; and

Z is substitued or unsubstituted

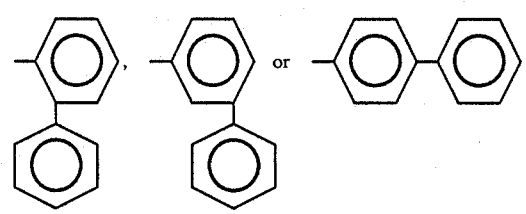

wherein the permissible substituents are one or more halo, $C_{1-6}$ alkyl, alkoxy, polyhaloalkyl, polyhaloalkoxy, nitro, cyano, carboxylic acid, carboxylic acid salt or carboxylic acid ester substituents which may be the same or different.

The novel compounds of this invention are illustrated by, but not limited to, the following:

1-(2,6-difluorobenzoyl)-3-[3-methyl-5-chlorl-4-(2-phenylphenoxy)phenyl]urea;

1-(2,6-difluorobenzoyl)-3-[3,5-dimethyl-4-(2-phenyl-4-bromophenoxy)phenyl]urea;

1-(2-chlorobenzoyl)-3-[3,5-dimethyl-4-(2-phenyl-4-bromophenoxy)phenyl]urea;

1-(2,6-difluorobenzoyl)-3-[2,5-dimethyl-3-chloro-4-(2-phenyl-4-methylphenoxy)phenyl]urea;

1-(2-trifluoromethoxybenzoyl)-3-[2,5-dimethyl-3-chloro-4-(2-phenyl-4-methylphenoxy)phenyl]urea;

1-(2-chlorobenzoyl)-3-[2,5-dimethyl-3-chloro-4-(2-phenyl-4-trifluoromethylphenoxy)phenyl]urea;

1-(2-chlorobenzoyl)-3-[3-trifluoromethyl-4-(2-phenyl-
  phenoxy)phenyl]urea;
1-(2-nitrobenzoyl)-3-[3-methoxy-4-(2-phenyl-4-ethox-
  ycarbonylphenoxy)phenyl]urea;
1-(2-chlorobenzoyl)-3-[3-ethoxycarbonyl-4-(2-phenyl-
  4-bromophenoxy)phenyl]urea;
1-(2,6-difluorobenzoyl)-3-[2,5-dimethyl-3-chloro-4-(2-
  phenyl-4-cyanophenoxy)phenyl]urea;
1-(2,6-difluorobenzoyl)-3-[3,5-dichloro-4-[4-(2-phenyl-
  4-chlorophenyl)butoxy]phenyl]urea;
1-(2-chlorobenzoyl)-3-[3-carboxy-4-(2-phenyl-4-chloro-
  phenoxy)phenyl]urea;
1-(2,6-difluorobenzoyl)-3-[3,5-dichloro-4-[alpha, alpha-
  dimethyl-2-phenyl-4-chlorobenzyloxy]phenyl]urea;
1-(2-chlorobenzoyl)-3-[2,5-dimethyl-3-chloro-4-(2-phe-
  nyl-4-chlorophenoxy)phenyl]urea;
1-(2,6-difluorobenzoyl)-3-[2,5-dimethyl-3-chloro-4-(2-
  phenyl-4-chlorophenoxy)phenyl]urea;
1-(2-chloro-6-fluorobenzoyl)-3-[2,5-dimethyl-3-chloro-
  4-(2-phenylphenoxy)phenyl]urea;
1,(2,6-difluorobenzoyl)-3-[3,5-dichloro-4-(2-phenyl-
  phenylmethoxy)phenyl]urea;
1-(2,6-difluorobenzoyl)-3-[2,5-dimethyl-3-chloro-4-(2-
  phenylphenoxy)phenyl]urea;
1-(2-chlorobenzoyl)-3-[2,5-dimethyl-3-chloro-4-(2-
  phenylphenoxy)phenyl]urea;
1-(2,6-difluorobenzoyl)-3-[3,5-dichloro-4-(alpha-meth-
  yl-(2-phenylbenzyloxy))phenyl]urea;
1-(2-chlorobenzoyl)-3-[3,5-dichloro-4-(alpha-methyl-(2-
  phenylbenzyloxy))phenyl]urea;
1-(2-trifluoromethylbenzoyl)-3-[2,5-dimethyl-3-chloro-
  4-(2-phenyl-4-chlorophenoxy)phenyl]urea;
1-(2-methoxybenzoyl)-3-[2,5-dimethyl-3-chloro-4-(2-
  phenyl-4-chlorophenoxy)phenyl]urea;
1-(2-ethoxybenzoyl)-3-[2,5-dimethyl-3-chloro-4-(2-
  phenylphenoxy)phenyl]urea;
1-(2-fluorobenzoyl)-3-[3-methoxy-5-chloro-4-(2-phe-
  nyl-4-chlorophenoxy)phenyl]urea;
1-(2,6-difluorobenzoyl)-3-[3-trifluoromethoxy-4-(2-phe-
  nyl-4-methoxyphenoxy)phenyl]urea;
1-(2,6-difluorobenzoyl)-3-[2,5-dimethyl-3-chloro-4-(2-
  phenyl-4-trifluoromethoxyphenoxy)phenyl]urea;
1-(2-fluorobenzoyl)-3-[2,5-dimethyl-3-chloro-4-(2-phe-
  nyl-4-cyanophenoxy)phenyl]urea;
1-(2,6-difluorobenzoyl)-3-[3,5-dichloro-4-(2-phenyl-4-
  nitrophenoxy)phenyl]urea;
1-(2,6-difluorobenzoyl)-3-[2,5-dimethyl-3-chloro-4-(3-
  phenylphenoxy)phenyl]urea;
1-(2,6dichlorobenzoyl)-3-[3,5-dichloro-4-(2-phenyl-4-
  carboxyphenoxy)phenyl]urea;
1-(2,6-difluorobenzoyl)-3-[2,5-dimethyl-3-chloro-4-(2-
  bromo-4-phenylphenoxy)phenyl]urea;
1-(2-chlorobenzoyl)-3-[2,5-dimethyl-3-chloro-4-(2-
  phenylphenoxy)phenyl]thiourea;
1-(2-fluorobenzoyl)-3-[3-nitro-4-(2-phenyl-4-chloro-
  phenoxy)phenyl]urea;
1-(2-fluorobenzoyl)-3-[2,5-dimethyl-3-chloro-4-(2-
  phenylphenoxy)phenyl]thiourea;
1-(2-fluorobenzoyl)-3-(2,5-dimethyl-3-chloro-4-(2-phe-
  nyl-4-chlorophenoxy)phenyl]urea;
1-(2-ethoxybenzoyl)-3-[3-chloro-5-ethyl-4-(2-phenyl-4-
  tert-butylphenoxy)phenyl]urea;
1-(2-isopropylbenzoyl)-3-[2,5-dimethyl-3-carboxy-4-(2-
  phenyl-4-carboxyphenoxy)phenyl]urea dissodium
  salt;
1-(2,6-difluorobenzoyl)-3-[3-cyano-5-chloro-4-(2-phe-
  nyl-4-chlorophenoxy)phenyl]urea;

1-(2,6-difluorobenzoyl)-3-[3-isopropyl-5-methyl-4-(2-
  phenyl-4-ethoxyphenoxy)phenyl]urea;
1-(2,6-difluorobenzoyl)-3-[2-methyl-5-chloro-4-(2-
  phenylphenoxy)phenyl]urea; and
1-(2,6-difluorobenzoyl)-3-[2,5-dimethyl-3-chloro-4-(2-
  (4-chlorophenyl)phenoxy)phenyl]urea.

The novel biphenylyloxy and biphenylylalkoxy aryl acyl urea compounds of this invention can be prepared by one or more methods. For example, the compounds of this invention can be prepared by reacting a substituted phenylisocyanate or phenyl isothiocyanate 2 with a benzamide 1 as follows:

SCHEME I

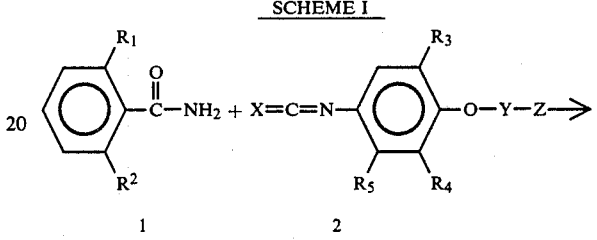

wherein $R_1$, $R_2$, $R_3$, $R_4$, $R_5$, X, Y and Z are as hereinbefore described.

Alternatively, the novel compounds of this invention can be prepared by the reaction of an acyl halide 3 with a substituted urea of thiourea 4 as follows:

SCHEME II

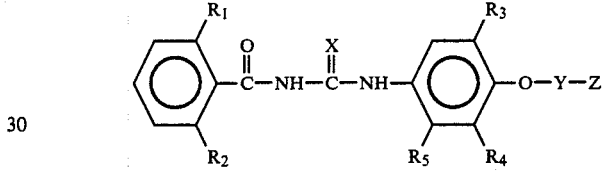

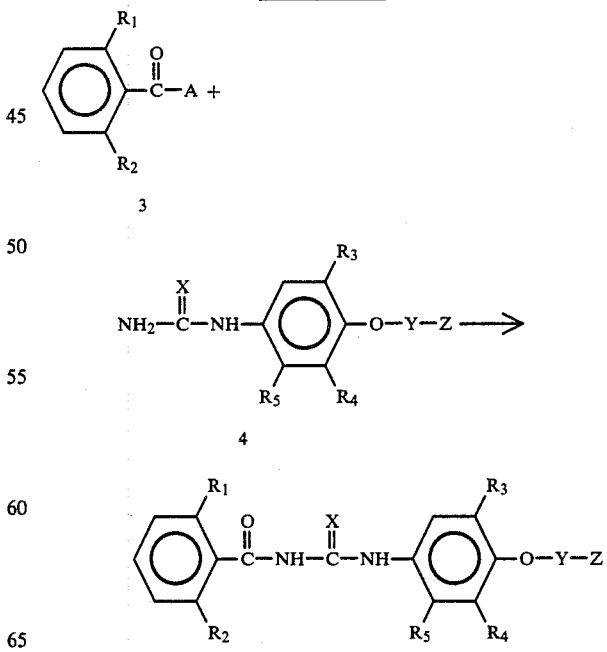

wherein A is halogen and $R_1$, $R_2$, $R_3$, $R_4$, $R_5$, X, Y and Z are as hereinbefore described.

The novel compounds of this invention can also be prepared by reacting a substituted aniline 6 with a acyl isocyanates or acyl isothiocyanate 5 as follows:

SCHEME III

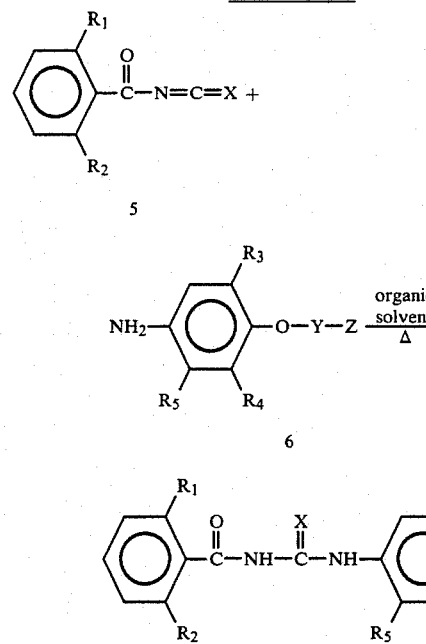

wherein $R_1$, $R_2$, $R_3$, $R_4$, $R_5$, X, Y and Z are as hereinbefore described.

In general, the reactions illustrated in Schemes I, II, and III can be carried out in organic solvents such as aromatic hydrocarbons, halogenated hydrocarbons or ethers. Solvents like toluene, 1,2-dichloroethane and p-dioxane are preferred. The reactions in general proceed at temperatures ranging from about ambient temperature to about 100° C.

The intermediates shown in Schemes I, II, and III can be prepared according to generally accepted procedures. Thus, the substituted acyl isocyanate 5 (X=O) can be prepared from the corresponding benzamide according to the general procedure of Speziale et. al., *J. Org. Chem.*, 27, 3742 (1962) as follows:

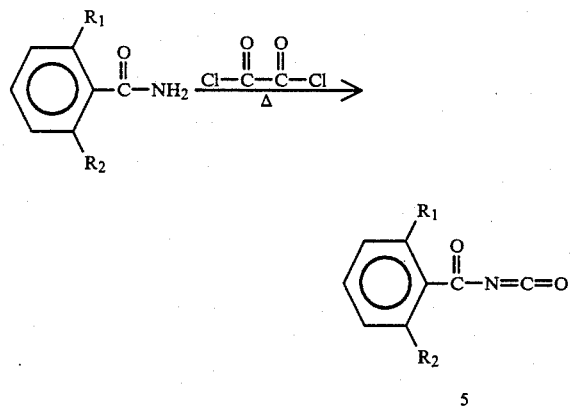

The substituted acyl isothiocyanate 5 (X=S) can be prepared by reacting a acyl chloride with potassium thiocyanate according to the procedure of Ambelang et. al. *J. Amer. Chem. Soc.* 61, 632 (1939) as follows:

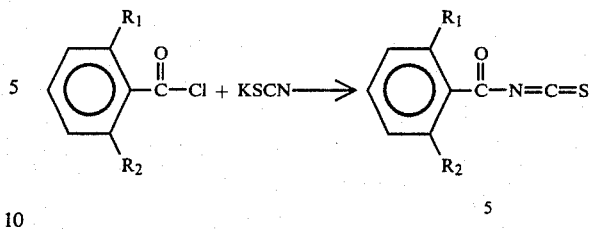

The aniline compounds of the type 6 can be prepared as follows:

SCHEME IV

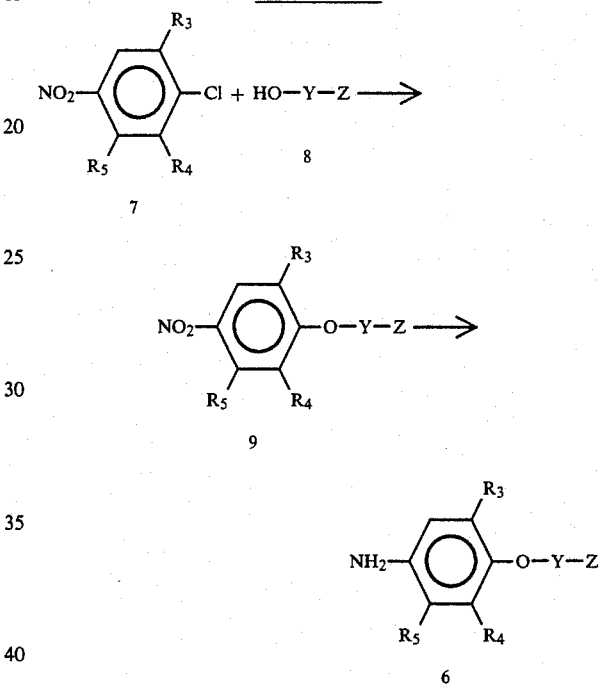

wherein $R_3$, $R_4$, $R_5$, Y and Z are as hereinbefore described.

The reaction of substituted phenol 8 (Y-covalent bond) with chloronitrobenzene 7 to give nitro ether 9 proceeds in the presence of a base in an inert solvent at elevated temperature. The bases suitable for this reaction are potassium carbonate, sodium hydride, potassium hydroxide and sodium hydroxide. Suitable solvents are acetone, toluene, dimethylformamide, and dimethylsulfoxide. The above reaction can also be achieved biphasely in the presence of a phase-transfer catalyst.

The reduction of nitro ether 9 to aniline 6 can be achieved by hydrogenation using a catalytic amount of platinum or palladium on carbon under pressure, ranging from 20–100 psi at ambient temperature. Suitable solvents for hydrogenation include aromatic hydrocarbons or alcohols. The reduction can also be achieved by a chemical method using the procedure described in United Kingdom Pat. No. 1,456,964 to E. Endus et. al.

Isocyanate or isothiocyanate 2 can be obtained by reacting the substituted aniline 6 with phosgene or thiophosgene. Urea or thiourea 4 can be obtained by the treatment of 2 with ammonium hydroxide. These procedures are depicted as follows:

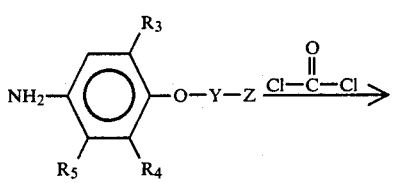

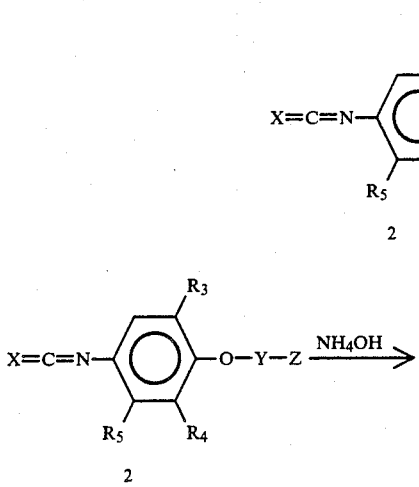

wherein $R_3$, $R_4$, $R_5$, X, Y and Z are as hereinbefore described.

Benzamide 1 and acyl halide 3 are available commercially or can be prepared by conventional methods known in the art.

Other intermediates which are useful in the preparation of the novel compounds of this invention can be prepared by known methods.

4-Bromo-2-phenylphenol can be obtained by the reaction of 2-phenylphenol with N-bromosuccinimide in dimethylformamide at room temperature for 24 hours as described by R. H. Mitchell, Y. H. Lai and R. V. Williams, *J. Org. Chem.* 44, 4733 (1979) as follows:

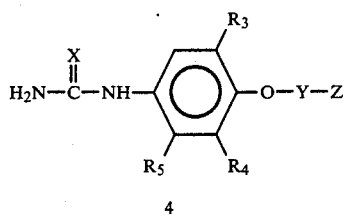

2-Nitro-4,5-dichlorotoluene can be obtained by the reaction of 3,4-dichlorotoluene using 90% nitric acid as follows:

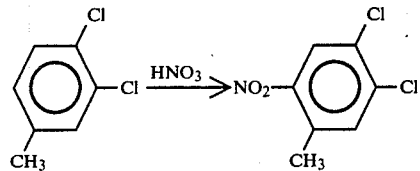

Another intermediate 2,5-dimethyl-3,4-dichloronitrobenzene can be obtained by the reactions as follows:

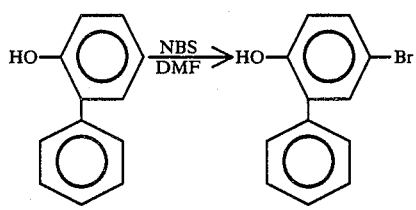

The compounds contemplated in this invention may be applied as pesticides according to methods known to those skilled in the art. Pesticidal compositions containing the compounds as the active toxicant will usually comprise a carrier and/or diluent, either liquid or solid.

Suitable liquid diluents or carriers include water, petroleum distillates, or other liquid carriers with or without surface active agents. Liquid concentrates may be prepared by dissolving one of these compounds with a nonphytotoxic solvent such as acetone, xylene, dimethylformamide or nitrobenzene and dispersing the toxicants in water with the acid of suitable surface active emulsifying and dispersing agents.

The choice of dispersing and emulsifying agents and the amount employed is dictated by the nature of the composition and the ability of the agent to facilitate the dispersion of the toxicant. Generally, it is desirable to use as little of the agent as is possible, consistent with the desired dispersion of the toxicant in the spray so that rain does not re-emulsify the toxicant after it is applied to the plant and wash it off the plant. Nonionic, anionic, or cationic dispersing and emulsifying agents may be employed, for example, the condensation products of alkylene oxides with phenol and organic acids, alkyl aryl sulfonates, complex ether alcohols, quaternary ammonium compounds, and the like.

In the preparation of wettable powder or dust or granulated compositions, the active ingredient is dispersed in and on an appropriately divided solid carrier such as clay, talc, bentonite, diatomaceous earth, fullers earth, and the like. In the formulation of the wettable powders the aforementioned dispersing agents as well as lignosulfonates can be included.

The required amount of the toxicants contemplated herein may be applied per acre treated in from 1 to 200 gallons or more of liquid carrier and/or diluent or in from about 5 to 500 pounds of inert solid carrier and/or diluent. The concentration in the liquid concentration will usually vary from about 10 to 95 percent by weight and in the solid formulations from about 0.5 to about 90 percent by weight. Satisfactory sprays, dusts, or granules for general use contain from about ¼ to 15 pounds of active toxicant per acre.

The pesticides contemplated herein prevent attack by insects and mites upon plants or other material to which the pesticides are applied, and they have relatively high residual toxicity. With respect to plants, they have a high margin of safety in that when used in sufficient amount to kill or repel the pests, they do not burn or injure the plant, and they resist weathering which includes wash-of caused by rain, decomposition by ultraviolet light, oxidation, or hydrolysis in the presence of moisture or, at least, such decomposition, oxidation, and hydrolysis as would materially decrease the desirable pesticidal characteristic of the toxicants or impart undesirable characteristics, for instance, phytotoxicity, to the toxicants. The toxicants are so chemically inert that they are not compatible with substantially any other constituents of the spray schedule, and they may be used in the soil, upon the seeds, or the roots of plants without injuring either the seeds or roots of plants.

Mixtures of the active compounds may be employed if desired as well as combinations of the active compounds of this invention with other biologically active compounds or synergists.

The following examples are illustrative of methods utilized in the preparation of compounds of this invention.

EXAMPLE 1

Part A: Preparation of 4-(2-chloro-4-phenylphenoxy)-2,5-dimethyl-3-chloronitrobenzene Into a 100 milliliter round bottom flask equipped with a thermometer, magnetic stirrer and condenser was added 12.0 grams (0.054 moles) of 2,5-dimethyl-3,4-dichloronitrobenzene, 14.5 grams (0.071 moles) of 2-chloro-4-phenylphenol, 12.0 grams (0.087 moles) of potassium carbonate and 20 milliliters of dimethylformamide (DMF) under a nitrogen atmosphere at ambient temperature. The reaction mixture was then heated in an oil bath at a temperature of 110° C.–120° C. for a period of 72 hours. After cooling to ambient temperature, the reaction mixture was filtered through celite and concentrated (DMF removed under vaccum) to give an amber oil. The amber oil was dissolved in toluene and thereafter washed once with 4% sodium hydroxide, once with water and finally once with a saturated aqueous sodium chloride solution. The amber oil was then dried over sodium sulfate, concentrated (toluene removed under vacuum) and stirred into a hexane-ethyl acetate mixture (6:1 volume ratio). Crystallization from the hexane-ethyl acetate mixture and filtration afforded 15.02 grams of a tan powder having a melting point of 92.5° C.–94.0° C. Elemental analysis of the tan powder indicated the following:

Analysis: $C_{20}H_{15}Cl_2NO_3$.
Calculated: C, 61.87; H, 3.89; N, 3.61.
Found: C, 62.14; H, 4.05; N, 3.65.

Part B: Preparation of 4-(2-chloro-4-phenylphenoxy)-2,5-dimethyl-3-chloroaniline A 500 milliliter rocking Parr hydrogenator was charged with a solution of 13.5 grams (0.035 moles) of 4-(2-chloro-4-phenylphenoxy)-2,5-dimethyl-3-chloronitrobenzene prepared in Part A and 135 milliliters of toluene. To this solution was added 1.0 gram of a catalyst of 5% platinum on carbon and the reactor was sealed. The reactor was purged twice with nitrogen and then twice with hydrogen. Hydrogen was then introduced to a pressure of 31 psi and this pressure was maintained until the hydrogen up-take ceased, i.e., about 1.5 hours. The material was removed from the rector, filtered and concentrated (toluene removed under vacuum) to give a viscous oil. Crystallization from a hexane-ethyl acetate mixture afforded 10.6 grams of a tan powder having a melting point of 117° C.–119° C. Elemental analysis of the tan powder indicated the following:

Analysis: $C_{20}H_{17}Cl_2No$.
Calculated: C, 67.05; H, 4.78; N, 3.91.
Found: C, 66.91; H, 5.02; N, 3.83.

Part C: Preparation of 1-(2-chlorobenzoyl)-3-[2,5-dimethyl-3-chloro-4-(2-chloro-4-phenylphenoxy) phenyl]urea To a solution containing 1.61 grams (0.004 moles) of 4-(2-chloro-4-phenylphenoxy)-2,5-dimethyl-3-chloroaniline prepared in Part B and 3 milliliters of toluene, which solution was warmed to 40° C.–50° C. and placed under an atmosphere of nitrogen, was added a solution containing 0.98 grams (0.005 moles) of 2-chlorobenzoyl isocyanate and 0.05 milliliters of toluene. The resulting mixture was then heated to a temperature of 60° C.–70° C, for a period of 0.5–1.0 hours. After cooling to ambient temperature, the reaction mixture was diluted with 4 milliliters of toluene and 2 milliliters of hexane. This mixture was then filtred to give a solid material. The solid material was washed once with a toluene-hexane mixture (1:2 volume ratio) and finally once with hexane and then dried overnight in a vaccum oven at 50° C. This afforded a tan powder material having a melting point of 198° C.–199° C. Elemental analysis of the tan powder indicated the following:

Analysis: $C_{28}H_{21}Cl_3NO_2O_3$.
Calculated: C, 62.30; H, 3.92; N, 5.19.
Found: C, 62.46; H, 4.08; N, 5.14.

EXAMPLE 2

Part A: Preparation of 3,5-dichloro-4-(2-phenylphenylmethoxy)nitrobenzene

Into a 250 milliliter reaction flask equipped with a magnetic stirrer was added 10.04 grams (0.044 moles) of 3,4,5-trichloronitrobenzene, 8.16 grams (0.044 moles) of 2-phenylbenzyl alcohol, 1.29 grams (0.004 moles) of tetra-N-butylammonium bromide, 80 milliliters of toluene and aqueous sodium hydroxide (5.28 grams in 6.6 milliliters of water). The resulting mixture was stirred vigorously at ambient temperature overnight. The mixture was then diluted with water and filtered. The layers were separated and the organic layer was washed twice with water and finally once with a saturated aqueous sodium chloride solution. After drying over anhydrous sodium sulfate, the mixture was concentrated under vacuum to give a red-orange oil which was stirred into hexane. Crystallization from the hexane and filtration afforded a yellow-orange powder having a melting point of 83.0° C.–84.5° C.

Part B: Preparation of 3,5-dichloro-4-(2-phenylphenylmethoxy)aniline

A 500 milliliter rocking Parr hydrogenator was charged with a solution of 12 grams (0.032 moles) of 3,5-dichloro-4-(2-phenylphenylmethoxy) nitrobenzene prepared in Part A and 100 milliliters of toluene. To this solution was added 1.0 gram of a catalyst of 5% platinum on carbon and the reactor was sealed. The reactor was purged twice with nitrogen and then twice with hydrogen. Hydrogen was then introduced to a pressure of 26 psi and this pressure was maintained until the hydrogen up-take ceased, i.e., about 20 minutes. The material was removed from the reactor, filtered through celite and concentrated (toluene removed under vacuum) to give an oil. Crystallization from a hexane-ethyl acetate mixture (5:2 volume ratio) afforded 9.09 grams of an ivory powder having a melting point of 67.0° C.–69.0° C.

Part C: Preparation of 1-(2-chlorobenzoyl)-3-[3,5-dichloro-4-(2-phenylphenylmethoxy)phenyl]urea To a solution containing 1.55 grams (0.004 moles) of 3,5-dichloro-4-(2-phenylphenylmethoxy) aniline prepared in Part B and 5 milliliters of toluene, which solution was heated to a temperature of 60° C. and placed under an atmosphere of nitrogen, was added 0.98 grams (0.005 moles) of 2-chlorobenzoyl isocyanate. The resulting mixture was maintained at a temperature of 60° C. for a period of 0.5–1.0 hours. After cooling to ambient temperature, the reaction mixture was diluted with 1 milliliter of toluene. This mixture was then filtered to give a solid material. The solid material was washed once with toluene, once with a toluene-hexane mixture (1:1 volume ratio) and finally once with hexane and then dried overnight in a vacuum oven at 50° C. This afforded a white powder material having a melting point of 188.5° C.–192.0° C. Elemental analysis of the white powder indicated the following:

Analysis: $C_{27}H_{19}Cl_3N_2O_3$.
Calculated: C, 61.67; H, 3.64; N, 5.33.
Found: C, 61.28; H, 3.65; N, 5.16.

EXAMPLES 3 THROUGH 32

In a manner similar to that employed in the preceding Examples, and utilizing one of the synthesis schemes previously disclosed, other urea compounds were prepared. The identity of the substitutents on the generic formula and the analytical data are set forth in Table I below.

TABLE I

Biphenylyloxy and Biphenylylalkoxy Aryl Acyl Urea Compounds

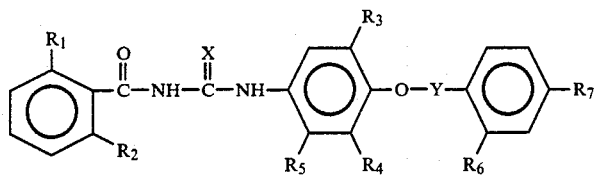

| Example | Molecular Formula | $R_1$ | $R_2$ | $R_3$ $R_4$ $R_5$ | $R_6$ | $R_7$ | X | Y | Calculated C | H | N | Found C | H | N |
|---|---|---|---|---|---|---|---|---|---|---|---|---|---|---|
| 3 | $C_{28}H_{22}Cl_2N_2O_3$ | Cl | H | 2,5-$(CH_3)_2$—3-Cl | Ph | H | O | Covalent Bond | 66.54 | 4.39 | 5.54 | 66.71 | 4.61 | 5.54 |
| 4 | $C_{28}H_{21}Cl_3N_2O_3$ | Cl | Cl | " | Ph | H | O | " | 62.30 | 3.92 | 5.19 | 62.44 | 4.09 | 5.17 |
| 5 | $C_{28}H_{21}Cl_2FN_2O_3$ | Cl | F | " | Ph | H | O | " | 64.26 | 4.04 | 5.35 | 64.53 | 4.14 | 5.31 |
| 6 | $C_{28}H_{21}ClF_2N_2O_3$ | F | F | " | Ph | H | O | " | 66.34 | 4.18 | 5.52 | 66.62 | 4.22 | 5.46 |
| 7 | $C_{28}H_{22}Cl_2N_2O_2S$ | Cl | H | " | Ph | H | S | " | 64.49 | 4.25 | 5.37 | 64.68 | 4.39 | 5.31 |
| 8 | $C_{28}H_{22}ClFN_2O_2S$ | F | H | " | Ph | H | S | " | 66.60 | 4.39 | 5.54 | 66.97 | 4.57 | 5.43 |
| 9 | $C_{29}H_{25}ClN_2O_2S$ | $(CH_3)$ | H | " | Ph | H | S | " | 69.59 | 5.03 | 5.59 | 70.51 | 5.27 | 5.25 |
| 10 | $C_{28}H_{22}Cl_2N_2O_3$ | Cl | H | " | H | Ph | O | " | 66.54 | 4.39 | 5.54 | 66.81 | 4.60 | 5.37 |
| 11 | $C_{28}H_{21}ClF_2N_2O_3$ | F | F | " | H | Ph | O | " | 66.34 | 4.18 | 5.52 | 66.30 | 4.38 | 5.34 |
| 12 | $C_{28}H_{22}Cl_2N_2O_2S$ | Cl | H | " | H | Ph | S | " | 64.49 | 4.25 | 5.37 | 64.44 | 4.38 | 5.29 |
| 13 | $C_{28}H_{21}BrCl_2N_2O_2S$ | Cl | H | " | Ph | Br | S | " | 56.02 | 3.52 | 4.67 | 55.88 | 3.73 | 4.65 |
| 14 | $C_{28}H_{20}Cl_2N_2O_3$ | F | F | " | Cl | Ph | O | " | 62.12 | 3.72 | 5.17 | 62.42 | 3.87 | 4.92 |
| 15 | $C_{28}H_{21}Cl_2FN_2O_3$ | F | H | " | Cl | Ph | O | " | 64.26 | 4.04 | 5.35 | 64.69 | 4.21 | 5.27 |
| 16 | $C_{28}H_{20}Cl_3FN_2O_3$ | Cl | F | " | Cl | Ph | O | " | 60.29 | 3.61 | 5.02 | 61.09 | 3.81 | 4.92 |
| 17 | $C_{28}H_{21}Cl_3N_2O_3$ | Cl | H | " | Ph | Cl | O | " | 62.30 | 3.92 | 5.19 | 63.20 | 4.00 | 5.47 |
| 18 | $C_{28}H_{21}Cl_2FN_2O_3$ | F | H | " | Ph | Cl | O | " | 64.26 | 4.04 | 5.35 | 65.61 | 4.18 | 5.41 |
| 19 | $C_{28}H_{20}Cl_3FN_2O_3$ | Cl | F | " | Ph | Cl | O | " | 60.29 | 3.61 | 5.02 | 60.83 | 3.79 | 5.06 |
| 20 | $C_{28}H_{20}Cl_2F_2N_2O_3$ | F | F | 2,5-$(CH_3)_2$3-Cl | Ph | Cl | O | " | 62.12 | 3.72 | 5.17 | 63.58 | 3.97 | 5.20 |
| 21 | $C_{27}H_{20}Cl_2N_2O_3$ | Cl | H | 2-$CH_3$5-Cl | Ph | H | O | " | 66.00 | 4.10 | 5.70 | 66.10 | 4.18 | 5.60 |
| 22 | $C_{27}H_{19}ClF_2N_2O_3$ | F | F | " | Ph | H | O | " | 65.80 | 3.88 | 5.68 | 66.31 | 4.06 | 5.40 |
| 23 | $C_{27}H_{20}Cl_2N_2O_2S$ | Cl | H | " | Ph | H | S | " | 63.91 | 3.97 | 5.52 | 64.03 | 4.26 | 5.86 |
| 24 | $C_{28}H_{21}BrCl_2N_2O_3$ | Cl | H | 2,5-$(CH_3)_2$—3-Cl | Ph | Br | O | " | 57.56 | 3.62 | 4.79 | 58.15 | 3.82 | 4.60 |
| 25 | $C_{28}H_{20}BrClF_2N_2O_3$ | F | F | " | Ph | Br | O | " | 57.41 | 3.44 | 4.78 | 57.85 | 3.59 | 4.91 |
| 26 | $C_{28}H_{20}BrCl_2FN_2O_3$ | Cl | F | " | Ph | Br | O | " | 55.84 | 3.35 | 4.65 | 55.87 | 3.36 | 4.55 |
| 27 | $C_{28}H_{20}ClF_3N_2O_3$ | $CF_3$ | H | " | Ph | H | O | " | 64.07 | 3.84 | 5.34 | 64.37 | 3.95 | 5.17 |
| 28 | $C_{27}H_{18}Cl_2F_2N_2O_3$ | F | F | 3,5-$Cl_2$ | Ph | H | O | $CH_2$ | 61.50 | 3.44 | 5.31 | 61.57 | 3.51 | 5.27 |
| 29 | $C_{27}H_{19}Cl_3N_2O_2S$ | Cl | H | " | Ph | H | S | $CH_2$ | 59.84 | 3.53 | 5.17 | 59.97 | 3.59 | 5.34 |
| 30 | $C_{28}H_{22}ClFN_2O_2S$ | F | H | 2,5-$(CH_3)_2$3-Cl | Ph | H | S | Covalent Bond | 66.60 | 4.39 | 5.54 | 67.04 | 4.64 | 5.54 |
| 31 | $C_{26}H_{16}Cl_2F_2N_2O_3$ | F | F | 3,5-$Cl_2$ | Ph | H | O | " | 60.84 | 3.14 | 5.46 | 60.40 | 3.20 | 5.38 |
| 32 | $C_{26}H_{17}Cl_3N_2O_3$ | Cl | H | " | Ph | H | O | " | 61.02 | 3.35 | 5.47 | 61.08 | 3.41 | 5.44 |

Ph = phenyl

Certain representative examples of the novel compounds of this invention were evaluated to determine their pesticidal activity against mites and certain insects, including a caterpillar and a beetle.

Suspension of the test compounds were prepared by dissolving one gram of compound in 50 milliliters of acetone in which had been dissolved 0.1 gram (10 percent of the weight of compound) of an alkylphenoxy polyethoxyethanol surfactant, as an emulsifying or dispersing agent. The resulting solution was mixed into 150 milliliters of water to give roughly 200 milliliters of a suspension containing the compound in finely divided form. The thus-prepared stock suspension contained 0.5 percent by weight of compound. The test concentrations in parts per million by weight employed in the tests described hereinbelow were obtained by appropriate dilutions of the stock suspension with water. Certain of the test compounds were also prepared by dissolving 375 mg of compound in 7.5 ml of dimethylformamide. Fifteen milliliters of acetone containing 37.5 mg (10 percent of the weight of test compound) of an alkylphenoxy polyethoxyethanol surfactant, as a wetting-/emulsifying/dispersing agent was added to the dimethylformamide solution. Fifty-two and one-half milliliters of water wasa mixed into the dimethylformamide-acetone mixture to give roughly 75 ml of a suspension containing the compound in solution or in finely divided form. The thus prepared stock suspension contained 0.5 percent by weight of compound. The test procedures were as follows:

Southern Armyworm Leaf Spray Bait Test

Larvae of the southern armyworm (Spodoptera eridania, (Cram.), reared on Tendergreen bean plants at a temperature of 80°±5° F. and a relative humidity of 50±5 percent, constituted the test insects.

The test compounds were formulated by diluting the stock suspension with water to give a suspension containing 500 parts of test compound per million parts of final formulation. Potted Tendergreen bean plants of standarad height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound was also sprayed on infested plants. When dry, the paired leaves were separated and each one was placed in a 9 centimeter Petri dish lined with moistened filter paper. Five randomly selected larvae were introduced into each dish and the dishes were closed. The closed dishes were labeled and held at 80°-85° F. for up to five days. Although the larvae could easily consume the whole leaf within twenty-four hours, no more food was added. Larvae which were unable to move the length of the body, even upon stimulation by prodding, were considered dead. Percent mortality was recorded for various concentration levels.

Mexican Bean Beetle Leaf Spray Test

Fourth instar larvae of the Mexican bean beetle (Epilachna varivestic, Muls.), reared on Tendergreen bean plants at a temperature of 80°±5° F. and 50±5 percent relative humidity, were the test insects. For certain of the tests second instar larvae (weighting about 6 mg) of the Mexican bean beetle (Epilachna varaivestis, Muls.), reared on Sieva Pole lime bean plants at a temperature of 80°±5° F. and 50±5 percent relative humidity, were the test insects.

The test compounds were formulated by diluting the stock suspension with water to give a suspension containing 500 parts of test compound per million parts of final formulation. Potted Tendergreen bean plants of standard height and age were placed on a revolving turntable and sprayed with 100-110 milliliters of test compound formulation by use of a DeVilbiss spray gun set at 40 psig air pressure. This application, which lasted 25 seconds, was sufficient to wet plants to run-off. As a control, 100-110 milliliters of a water-acetone-emulsifier solution containing no test compound was also sprayed on infested plants. When dry, the paired leaves were separated and each was placed in a 9 centimeter Petri dish lined with moistened filter paper. Five randomly selected larvae were introduced into each dish, and the dishes were closed. The closed dishes were labeled and held at a temperature of 80°±5° F., for five days. Although the larvae could easily consume the leaf within 24 to 48 hours, no more food was added. Larvae which were unable to move the length of the body, even upon stimulation, were considered dead. Percent mortality was recorded for various concentration levels.

Tobacco Budworm and Cotton Bollworm Leaf Spray Bait Test

Second instar larvae of the tobacco budworm (weighing about 4.5 mg) (Heliothis virescens, F.) and the cotton bollworm (weighing about 2.5 mg) (Heliothis zea, (Boddie)), obtained commercially and reared on artificial diet at a temperature of 80°±5° F. and a relative humidity of 50±5 percent, constituted the test insects.

Using a procedure similar to the above, but substituting cotton plants for snapbeans, treated and dried cotton leaves were introduced into 9 cm Petri dishes which were organized into groups of 10-dish sets. One randomly selected larvae was introduced into each dish of a ten dish set and the dishes were closed. The closed dishes were labelled and held at 80°±5° F. for five days. Larvae which were unable to move the length of the body, even upon stimulation, were considered dead. Percent mortality was recorded for various concentration levels. $LC_{50}$ or concentration required to kill 50 percent of the larvae was determined from the mortality figures.

Mite Larvacidal Test Method

The eggs of the two-spotted mite (Tetranychus urticae (Koch) are obtained from adults reared on Tendergreen beans under controlled conditions (80°±5° F. and 50±5 percent relative humidity). Heavily infested leaves from the stock culture are placed on uninfested bean plants. Females are allowed to oviposit for a period of 24 hours, and the leaves of the plant are then dipped in a 1000 ppm solution of tetraethylpyrophosphate (TEPP) in order to kill the motile forms and prevent additional egg laying. TEPP does not affect the viability of the eggs. The TEPP treated mite infested plants are held at 80°±5° F. and 50±5 percent relative humidity until the eggs hatch in 3-4 days. Then the larvae are transferred to bean plants 6-8 inches in height. A sufficient number of larvae for testing (50-100) were transferred from TEPP treated leaves to the fresh plants in 24 hours.

Infested Tendergreen bean plants are placed on a revolving turntable. Test compounds are formulated with DMF, acetone, and a 3 to 1 mixture of Triton 172 and 152 (alkylphenoxy polyethoxyethanol surfactant mixture), respectively and then diluted in water to appropriate concentrations of chemical for application to the infested plants by use of a DeVilbiss spray gun with air pressure set at 40 pounds. The volume of 100 milliliters is sufficient to wet the plants to run off. A blank formulation is used for the control.

The treated plants are held at 80°±5° F. and 50±5 percent relative humidity for a period of five to six days, when mortality counts of the larvae are made.

The biological properties of certain representative examples of the compounds of this invention are set forth in Table II below.

TABLE II

Biological Properties of Representative Biphenylyloxy and Biphenylylalkoxy Aryl Acyl Urea Compounds

| Example | Activity at 500 ppm[3] | |
|---|---|---|
| | SAW[1] | MBB[2] |
| 1 | A | A |
| 2 | A | A |
| 3 | A | A |
| 4 | A | A |
| 5 | A | A |
| 6 | A | A |
| 7 | A | A |
| 8 | A | A |
| 9 | A | A |
| 10 | C | A |
| 11 | A | A |
| 12 | C | A |
| 13 | C | C |
| 14 | A | A |
| 15 | A | A |
| 16 | A | A |
| 17 | A | A |
| 18 | A | A |
| 19 | A | A |
| 20 | A | A |

TABLE II-continued

Biological Properties of Representative Biphenylyloxy and Biphenylylalkoxy Aryl Acyl Urea Compounds

| Example | Activity at 500 ppm[3] | |
|---|---|---|
| | SAW[1] | MBB[2] |
| 21 | A | A |
| 22 | A | A |
| 23 | A | A |
| 24 | A | C |
| 25 | A | A |
| 26 | A | A |
| 27 | C | C |
| 28 | A | A |
| 29 | A | A |
| 30 | C | C |
| 31 | A | A |
| 32 | A | A |

[1]Southern Armyworm
[2]Mexican Bean Beetle
[3]Code:
A = 71–100% Kill
B = 31–70% Kill
C = 0–30% Kill

EXAMPLES 33 THROUGH 35 AND COMPARATIVE EXAMPLES A THROUGH H

In order to demonstrate the enhanced biological activity against the Southern Armyworm, representative biphenylyloxy and biphenylylalkoxy aryl acyl urea compounds were compared with known products. The results are set forth in Table III below.

TABLE III

Comparison of Representative Biphenylyloxy and Biphenylylalkoxy Aryl Acyl Urea Compounds with Known Compounds Against Southern Armyworm

| Example/Comparative Example | Compound | Application Rate (ppm) | Percent Control (after 5 days) |
|---|---|---|---|
| A | 2,6-difluorobenzoyl—NH—CO—NH—(4-chlorophenyl) | 10 | 100 |
| | | 5 | 40 |
| B | 2-chlorobenzoyl—NH—CO—NH—(3-chloro-4-(2,4-dimethylphenoxy)phenyl) | 125 | 100 |
| | | 21 | 30 |
| | | 8 | 20 |
| 33 | 2,6-difluorobenzoyl—NH—CO—NH—(2,6-dimethyl-3-chloro-4-(2-phenylphenoxy)phenyl) | 8 | 100 |
| | | 2 | 100 |

TABLE III-continued
Comparison of Representative Biphenylyloxy and Biphenylylalkoxy Aryl Acyl Urea Compounds with Known Compounds Against Southern Armyworm
| Example/ Comparative Example | Compound | Application Rate (ppm) | Percent Control (after 5 days) |
|---|---|---|---|
| 34 | 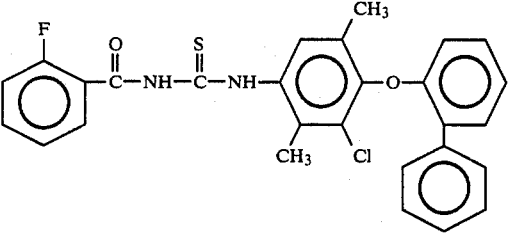 | 8<br>2 | 100<br>100 |
| 35 | 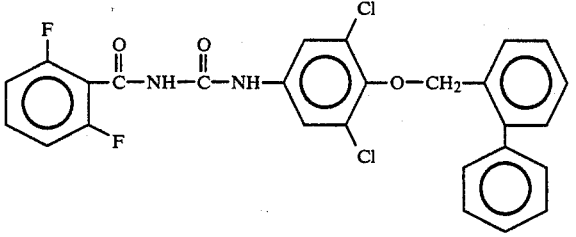 | 4<br>1 | 100<br>100 |
| C | 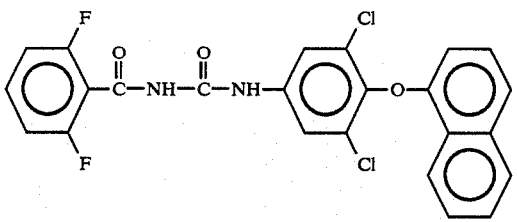 | 125<br>31<br>8 | 100<br>40<br>0 |
| D | 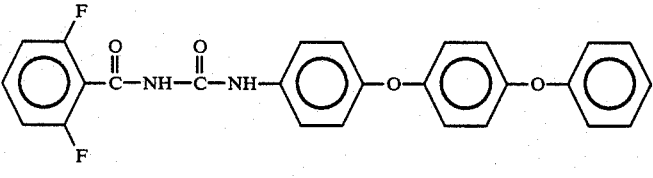 | 100<br>25 | 0<br>0 |
| E | 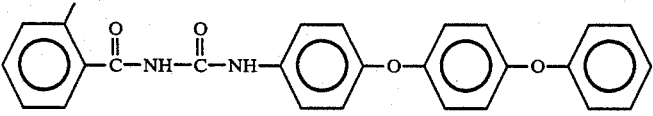 | 100<br>25 | 0<br>0 |
| F | 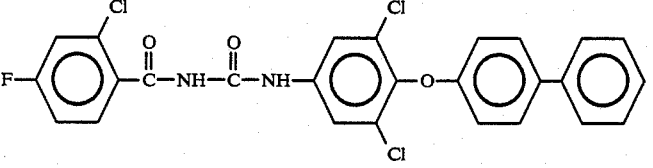 | 100<br>25<br>6.5 | 0<br>0<br>0 |
| G | 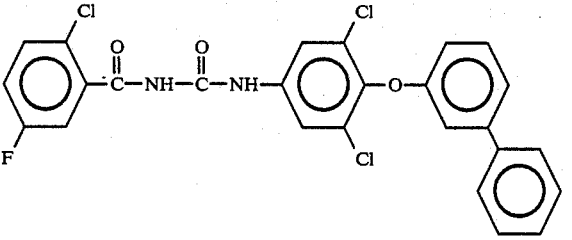 | 100<br>25<br>6.25 | 0<br>0<br>0 |

TABLE III-continued

Comparison of Representative
Biphenylyloxy and Biphenylylalkoxy Aryl
Acyl Urea Compounds with Known Compounds Against
Southern Armyworm

| Example/ Comparative Example | Compound | Application Rate (ppm) | Percent Control (after 5 days) |
|---|---|---|---|
| H | 2-Cl-C6H4-C(O)-NH-C(O)-NH-[2,6-(CH3)2-3-Cl-C6H2]-O-C6H4-SO2-C6H4-Cl | 8<br>4<br>2 | 10<br>0<br>0 |

As used in Table III, the compound of Comparative Example A is Dimilin ® which is commercially available from Philips Duphar Company (Netherlands). The compound of Comparative Example B was prepared in a manner similar to the procedure described in German Patent Application No. DE 3,104,407. The compound of Comparative Example C was prepared in a manner sililar to the procedure described in U.S. Pat. No. 4,426,385. The compounds of Comparative Examples D and E were prepared in a manner similar to the procedure described in German Patent Application No. De 3,104,407 and European Patent Application Publication No. 0057888. The compound of Comparative Example F was prepared in a manner similar to the procedure described in German Patent Application No. DE 3,217,619. The compound of Comparative Example G was prepared in a manner similar to the procedure described in European Patent Application Publication No. 0093977. The compound of Comparative Example H was prepared in a manner similar to the procedure described in copending U.S. patent application Ser. No. 454,849, filed Dec. 30, 1982.

EXAMPLES 36 THROUGH 39 AND COMPARATIVE EXAMPLES I THROUGH K

In order to demonstrate the enhanced biological activity against Heliothis ssp., representative biphenylyloxy and biphenylyalkoxy aryl acyl urea compounds were compared with known products. The results are set forth in Table IV below.

TABLE IV

Comparison of Representative
Biphenylyloxy and Biphenylylalkoxy Aryl Acyl Urea
Compounds with Known Compounds Against Heliothis

| Example/ Comparative Example | Compound | LC$_{50}$ values in ppm | |
|---|---|---|---|
| | | Heliothis Zea | Heliothis Virescens |
| I | 2,6-F2-C6H3-C(O)-NH-C(O)-NH-C6H4-Cl | 500 | 31 |
| J | 2,6-F2-C6H3-C(O)-NH-C(O)-NH-C6H4-O-[2,6-(CH3)2-Cl-C6H2]-CH3 | >100 | >100 |
| 36 | 2,6-F2-C6H3-C(O)-NH-C(O)-NH-[2,6-(CH3)2-Cl-C6H2]-O-C6H4-C6H5 | 2.2 | 9 |

TABLE IV-continued
Comparison of Representative Biphenylyloxy and Biphenylylalkoxy Aryl Acyl Urea Compounds with Known Compounds Against Heliothis

| Example/Comparative Example | Compound | LC$_{50}$ values in ppm Heliothis Zea | Heliothis Virescens |
|---|---|---|---|
| 37 | [2-Cl-benzoyl-NH-CO-NH-(2,6-diCH$_3$-3-Cl-4-(2-biphenylyloxy)phenyl)] | 1.7 | 4 |
| 38 | [2,6-diF-benzoyl-NH-CO-NH-(2,6-diCH$_3$-3-Cl-4-(4'-Cl-2-biphenylyloxy)phenyl)] | 1.6 | 1.9 |
| 39 | [2,6-diF-benzoyl-NH-CO-NH-(3,5-diCl-4-(2-biphenylylmethoxy)phenyl)] | 5 | 16 |
| K | [2,6-diF-benzoyl-NH-CO-NH-(3,5-diCl-4-(1-naphthyloxy)phenyl)] | 30 | 500 |

As used in Table IV, the compound of Comparative Example I is Dimilin ® as described hereinabove. The compound of Comparative Example J was prepared in a manner similar to the procedure described in German Patent Application No. DE 3,104,407. The compound of Comparative Example K was prepared in a manner similar to the procedure described in U.S. Pat. No. 4,426,385.

EXAMPLE 40

In order to demonstrate biological activity against the two-spotted mite *Tetranychus urticae* (Koch), a representative compound of this invention was tested. The results are set forth in Table V below.

TABLE V
Activity of Representative Biphenylyloxy or Biphenylylalkoxy Aryl Acyl Urea Compound Against Two Spotted Mite

| Example | Compound | Mortality Rating at 500 ppm(1) Larvae |
|---|---|---|
| 40 | [2-Cl-6-F-benzoyl-NH-CO-NH-(2,6-diCH$_3$-3-Cl-4-(2-biphenylyloxy)phenyl)] | A |

(1)Code:
A = 71–100% Kill
B = 31–70% Kill
C = 0–30% Kill

Although the invention has been illustrated by the preceding examples, it is not to be construed as being limited to the materials employed therein; but rather, the invention encompasses the generic area as hereinbefore disclosed. Various modifications and embodiments can be made without departing from the spirit and scope thereof.

We claim:

1. A compound of the formula:

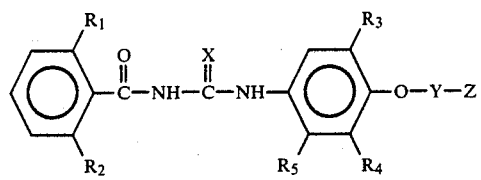

wherein:
$R_1$ is halogen, $C_{1-6}$ alkyl, alkoxy, polyhaloalkyl, polyhaloalkoxy or nitro;
$R_2$ is hydrogen, halogen, $C_{1-6}$ alkyl, alkoxy, polyhaloalkyl, polyhaloalkoxy or nitro;
$R_3$, $R_4$, and $R_5$ are independently hydrogen, halogen, $C_{1-6}$ alkyl, alkoxy, polyhaloalkyl, polyhaloalkoxy, nitro, cyano, carboxylic acid, carboxylic acid salt or carboxylic acid ester;
X is oxygen or sulfur;
Y is $C_{1-8}$ alkylene or a covalent bond; and
Z is substituted or unsubstituted

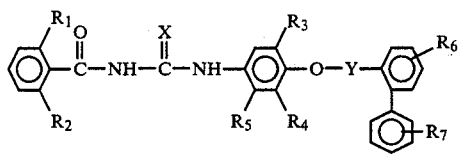

wherein the permissible substituents are one or more halo, $C_{1-6}$ alkyl, alkoxy, polyhaloalkyl, polyhaloalkoxy, nitro, cyano, carboxylic acid, carboxylic acid salt or carboxylic acid ester substituents which may be the same or different.

2. The compound of claim 1 wherein the formula is:

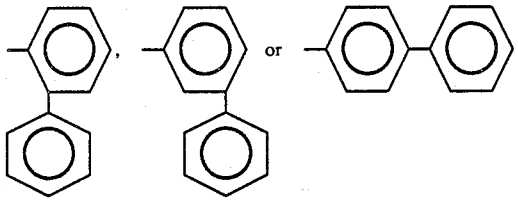

wherein:
$R_1$ is halogen, $C_{1-6}$ alkyl, alkoxy, polyhaloalkyl, polyhaloalkoxy or nitro;
$R_2$ is hydrogen, halogen, $C_{1-6}$ alkyl, alkoxy, polyhaloalkyl, polyhaloalkoxy or nitro;
$R_3$, $R_4$, $R_5$, $R_6$ and $R_7$ are independently hydrogen, halogen, $C_{1-6}$ alkyl, alkoxy, polyhaloalkyl, polyhaloalkoxy, nitro, cyano, carboxylic acid, carboxylic acid salt or carboxylic acid ester, provided at least one of $R_3$, $R_4$ and $R_5$ is other than hydrogen;
X is oxygen or sulfur; and
Y is $C_{1-8}$ alkylene or a covalent bond.

3. The compound of claim 1 wherein the formula is:

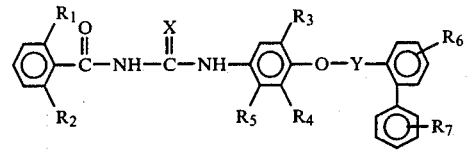

wherein:
$R_1$ is halogen, $C_{1-6}$ alkyl, alkoxy, polyhaloalkyl, polyhaloalkoxy or nitro;
$R_2$ is hydrogen, halogen, $C_{1-6}$ alkyl, alkoxy, polyhaloalkyl, polyhaloalkoxy or nitro;
$R_3$, $R_4$, $R_5$, $R_6$ and $R_7$ are independently hydrogen, halogen, $C_{1-6}$ alkyl, alkoxy, polyhaloalkyl, polyhaloalkoxy, nitro, cyano, carboxylic acid, carboxylic acid salt or carboxylic acid ester, provided at least two of $R_3$, $R_4$ and $R_5$ are other than hydrogen;
X is oxygen or sulfur; and
Y is $C_{1-8}$ alkylene or a covalent bond.

4. The compound of claim 1 wherein the formula is:

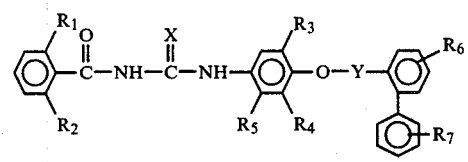

wherein:
$R_1$ is halogen, $C_{1-6}$ alkyl, alkoxy, polyhaloalkyl, polyhaloalkoxy or nitro;
$R_2$ is hydrogen, halogen, $C_{1-6}$ alkyl, alkoxy, polyhaloalkyl, polyhaloalkoxy or nitro;
$R_3$, $R_4$, Rhd 5, $R_6$ and $R_7$ are independently hydrogen, halogen, $C_{1-6}$ alkyl, alkoxy, polyhaloalkyl, polyhaloalkoxy, nitro, cyano, carboxylic acid, carboxylic acid salt or carboxylic acid ester, provided that $R_3$, $R_4$ and $R_5$ are other than hydrogen;
X is oxygen or sulfur; and
Y is $C_{1-8}$ alkylene or a covalent bond.

5. The compound of claim 1 wherein the formula is:

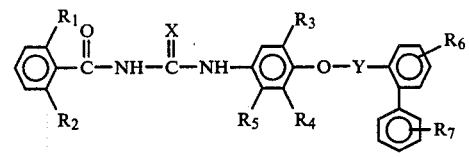

wherein:
$R_1$ and $R_2$ are independently halogen, $C_{1-6}$ alkyl, alkoxy, polyhaloalkyl, polyhaloalkoxy or nitro;
$R_3$, $R_4$, $R_5$, $R_6$ and $R_7$ are independently hydrogen, halogen, $C_{1-6}$ alkyl, alkoxy, polyhaloalkyl, polyhaloalkoxy, nitro, cyano, carboxylic acid, carboxylic acid salt or carboxylic acid ester, provided at least one of $R_3$, $R_4$ and $R_5$ is other than hydrogen;
X is oxygen or sulfur; and
Y is $C_{1-8}$ alkylene or a covalent bond.

6. The compound of claim 1 wherein the formula is:

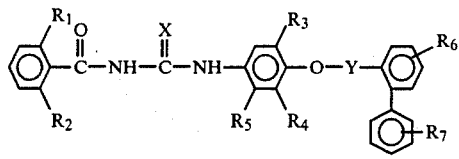

wherein:
R$_1$ and R$_2$ are independently halogen, C$_{1-6}$ alkyl, alkoxy, polyhaloalkyl, polyhaloalkoxy or nitro;
R$_3$, R$_4$, R$_5$, R$_6$ and R$_7$ are independently hydrogen, halogen, C$_{1-6}$ alkyl, alkoxy, polyhaloalkyl, polyhaloalkoxy, nitro, cyano, carboxylic acid, carboxylic acid salt or carboxylic acid ester, provided at least two of R$_3$, R$_4$ and R$_5$ are other than hydrogen;
X is oxygen or sulfur; and
Y is C$_{1-8}$ alkylene or a covalent bond.

7. The compound of claim 1 wherein the formula is:

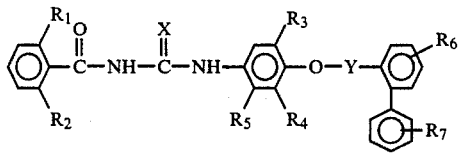

wherein:
R$_1$ and R$_2$ are independently halogen, C$_{1-6}$ alkyl, alkoxy, polyhaloalkyl, polyhaloalkoxy or nitro;
R$_3$, R$_4$, R$_5$, R$_6$ and R$_7$ are independently hydrogen, halogen, C$_{1-6}$ alkyl, alkoxy, polyhaloalkyl, polyhaloalkoxy, nitro, cyano, carboxylic acid, carboxylic acid salt or carboxylic acid ester, provided that R$_3$, R$_4$ and R$_5$ are other than hydrogen;
X is oxygen or sulfur; and
Y is C$_{1-8}$ alkylene or a covalent bond.

8. The compound of claim 1 which is 1-(2-chlorobenzoyl)-3-[2,5-dimethyl-3-chloro-4-(2-phenylphenoxy)-phenyl]urea.

9. The compound of claim 1 which is 1-(2,6-difluorobenzoyl)-3-[2,5-dimethyl-3-chloro-4-(2-phenylphenoxy)phenyl]urea.

10. The compound of claim 1 which is 1-(2-chlorobenzoyl)-3-[2,5-dimethyl-3-chloro-4-(2-phenyl-4-chlorophenoxy)phenyl]urea.

11. The compound of claim 1 which is 1-(2,6-difluorobenzoyl)3-[2,5-dimethyl-3-chloro-4-(2-phenyl-4-chlorophenoxy)phenyl]urea.

12. The compound of claim 1 which is 1-(2-chloro-6-fluorobenzoyl)-3-[2,5-dimethyl-3-chloro-4-(2-phenylphenoxy)phenyl]urea.

13. The compound of claim 1 which is 1-(2,6-difluorobenzoyl)-3-[3,5-dichloro-4-(2-phenylphenylmethoxy)phenyl]urea.

14. The compound of claim 1 which is 1-(2-fluorobenzoyl)-3-[2,5-dimethyl-3-chloro-4-(2-phenylphenoxy)-phenyl]urea.

15. The compound of claim 1 which is 1-(2-fluorobenzoyl)-3-[2,5-dimethyl-3-chloro-4-(2-phenylphenoxy)-phenyl]thiourea.

16. A pesticide composition comprising an acceptable carrier and a pesticidally effective amount of the compound of claim 1.

17. A pesticide composition comprising an acceptable carrier and a pesticidally effective amount of the compound of claim 2.

18. A pesticide composition comprising an acceptable carrier and a pesticidally effective amount of the compound of claim 3.

19. A pesticide composition comprising an acceptable carrier and a pesticidally effective amount of the compound of claim 4.

20. A pesticide composition comprising an acceptable carrier and a pesticidally effective amount of the compound of claim 5.

21. A pesticide composition comprising an acceptable carrier and a pesticidally effective amount of the compound of claim 6.

22. A pesticide composition comprising an acceptable carrier and a pesticidally effective amount of the compound of claim 7.

* * * * *